(12) United States Patent
Bian et al.

(10) Patent No.: US 9,775,857 B2
(45) Date of Patent: Oct. 3, 2017

(54) **LIGNANS ISOLATED FROM *LASIA SPINOSA* (L.) THWAIT**

(71) Applicant: Hong Kong Baptist University, Kowloon (HK)

(72) Inventors: Zhaoxiang Bian, Kowloon (HK); Huaixue Mu, Kowloon (HK); Chengyuan Lin, Kowloon (HK); Hongxi Xu, Kowloon (HK); Dajian Yang, Kowloon (HK); Shilin Chen, Kowloon (HK); Aiping Lu, Kowloon (HK); Albert Sun Chi Chan, Kowloon (HK)

(73) Assignee: HONG KONG BAPTIST UNIVERSITY, Kowloon Tong, Kowloon (HK)

( * ) Notice: Subject to any disclaimer, the term of this patent is extended or adjusted under 35 U.S.C. 154(b) by 0 days.

(21) Appl. No.: 15/190,587

(22) Filed: Jun. 23, 2016

(65) Prior Publication Data

US 2016/0375082 A1    Dec. 29, 2016

Related U.S. Application Data

(60) Provisional application No. 62/183,726, filed on Jun. 23, 2015.

(51) Int. Cl.
*A61K 36/00* (2006.01)
*A61K 31/7048* (2006.01)
*A61K 36/888* (2006.01)
*A61K 31/09* (2006.01)
*A61K 31/341* (2006.01)
*A61K 31/34* (2006.01)
*A61K 9/00* (2006.01)
*A61K 31/353* (2006.01)

(52) U.S. Cl.
CPC ........ *A61K 31/7048* (2013.01); *A61K 9/0019* (2013.01); *A61K 9/0053* (2013.01); *A61K 31/09* (2013.01); *A61K 31/34* (2013.01); *A61K 31/341* (2013.01); *A61K 31/353* (2013.01); *A61K 36/888* (2013.01)

(58) Field of Classification Search
CPC ..................................................... A61K 36/00
See application file for complete search history.

(56) References Cited

PUBLICATIONS

Hernandez-Ramirez et al, Dietary intake of polyphenols, nitrate and nitrite and gastric cancer risk in Mexico City. International journal of cancer, (Sep. 15, 2009) vol. 125, No. 6, pp. 1424-1430.*
Reagan-Shaw et al, "Dose translation from animal to human studies revisited," The FASEB Journal, Mar. 2007, pp. 659-661, vol. 22 Mar. 2007, the Federation of American Societies for Experimental Biology, Bethesda, Maryland, United States, 3 pages.

* cited by examiner

*Primary Examiner* — Qiuwen Mi
(74) *Attorney, Agent, or Firm* — Idea Intellectual Limited; Margaret A. Burke; Sam T. Yip

(57) ABSTRACT

The present invention relates to chemical constituents of the hydro-alcoholic extract of root of *Lasia spinosa* (L.) Thwait. More particularly, it relates to the bioactive chemical composition of *Lasia spinosa* (L.) Thwait and its anticancer effect. The present invention has application in the treatment of human esophageal carcinoma.

7 Claims, 7 Drawing Sheets

LIGNANS ISOLATED FROM *LASIA SPINOSA* (L.) THWAIT

CROSS-REFERENCE TO RELATED APPLICATIONS

This application claims the benefit of U.S. Provisional Patent Application Ser. No. 62/183,728 filed Jun. 23, 2015; 62/183,729 filed Jun. 23, 2015 and 62/183,726 filed Jun. 23, 2015; the disclosures of which are incorporated herein by reference in their entirety.

FIELD OF INVENTION

The present invention relates to chemical constituents of the hydro-alcoholic extract of root of *Lasia spinosa* (L.) Thwait. More particularly, it relates to the bioactive chemical composition of *Lasia spinosa* (L.) Thwait and its anti-cancer effect. The present invention has an application in the treatment of human esophageal carcinoma.

BACKGROUND OF INVENTION

Lignan and neolignans are major components of plants, accounting for 15-25% (w/w) of herbaceous biomass. Most of the lignans and neolignans in plants are optically active and exhibit important physiological functions in plant defense and human health. Lignans belong to a structurally diverse class of aromatic phenylpropanoid compounds which can be divided into five categories according to the skeleton structure, including dibenzocyclooctadiene, 2,3-dimethyl-1,4-diarylbutane, 4-aryltetralin, spirobenzofuranoid dibenzocyclooctadiene, and tetrahydrofuran.

*Lasia spinosa* (L.) Thwait from the family Araceae is a herbal medicine widely used in the southwest of China. However, there had little information about the details of the bioactive chemical composition of *Lasia spinosa* (L.) Thwait.

It is an objective of the present invention to provide chemical constituents of the hydro-alcoholic extract of root of *Lasia spinosa* (L.) Thwait and its anticancer effect.

To the best of the inventors' knowledge, the invention disclosed herein is novel and inventive over the prior art.

Citation or identification of any reference in this section or any other section of this application shall not be construed as an admission that such reference is available as prior art for the present application.

SUMMARY OF INVENTION

Accordingly, it is an objective of the invention to provide chemical constituents of the hydro-alcoholic extract of root of *Lasia spinosa* (L.) Thwait for exerting an anticancer effect and a treatment of an esophageal cancer.

In accordance with one aspect of the present invention, there is provided a method for inhibiting the growth of an esophageal carcinoma in a subject in need thereof by administering to said subject an effective amount of at least one compound selected from lyoniresinol (1), 5,5'-dimethoxy-secoiso-lariciresinol (2), 2-(4-hydroxy-3,5-dimethoxybenzyl)-3-(4-hydroxy-3-methoxybenzyl)-1,2-butanediol (3), (7'S,8S,8R)-4,4'-dihydroxy-3,3',5,5'-tetramethoxy-7',9-eproxylignan-9'-ol-7-one (4), 5,5'-dimethoxysecoiso-lariciresinol (5), secoisolariciresinol (6), 5'-methyoxlariciresinol (7), dihydrodehydrodiconifery alcohol (8) and syringaresinol (9), or a mixture thereof.

In a first embodiment of one aspect of the present invention, the compound is administered via intraperitoneal injection.

In a second embodiment of one aspect of the present invention, the effective amount is no more than 2.43 mg/kg per day.

In a third embodiment of one aspect of the present invention, the subject in need thereof is a human.

In accordance with a second aspect of the present invention, there is provided a method for inhibiting the growth of an esophageal carcinoma in a subject in need thereof by administering to said subject an effective amount of *Lasia spinosa* (L.) Thwait root or an extract from *Lasia spinosa* (L.) Thwait root.

In a first embodiment of second aspect of the present invention, the compound is administered via intraperitoneal injection.

In a second embodiment of second aspect of the present invention, the subject in need thereof is a mammal. Said mammal includes, but is not limited to a human.

Features, integers, characteristics, compounds, chemical moieties or groups described in conjunction with a particular aspect, embodiment or example of the invention are to be understood to be applicable to any other aspect, embodiment or example described herein unless incompatible therewith.

Those skilled in the art will appreciate that the invention described herein is susceptible to variations and modifications other than those specifically described.

The invention includes all such variation and modifications. The invention also includes all of the steps and features referred to or indicated in the specification, individually or collectively and any and all combinations or any two or more of the steps or features.

Throughout this specification, unless the context requires otherwise, the word "comprise" or variations such as "comprises" or "comprising", will be understood to imply the inclusion of a stated integer or group of integers but not the exclusion of any other integer or group of integers. It is also noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Furthermore, throughout the specification and claims, unless the context requires otherwise, the word "include" or variations such as "includes" or "including", will be understood to imply the inclusion of a stated integer or group of integers but not the exclusion of any other integer or group of integers.

Other definitions for selected terms used herein may be found within the detailed description of the invention and apply throughout. Unless otherwise defined, all other technical terms used herein have the same meaning as commonly understood to one of ordinary skill in the art to which the invention belongs.

Other aspects and advantages of the invention will be apparent to those skilled in the art from a review of the ensuing description.

BRIEF DESCRIPTION OF DRAWINGS

The above and other objects and features of the present invention will become apparent from the following description of the invention, when taken in conjunction with the accompanying drawings, in which.

DETAILED DESCRIPTION OF INVENTION

The present invention is not to be limited in scope by any of the specific embodiments described herein. The following embodiments are presented for exemplification only.

General Experimental Procedures

MTT (3-[4,5-dimethylthiazol-2-yl]-2,5-diphenyltetrazolium bromide) and DMSO (dimethyl sulfoxide), and all chemicals used were of HPLC grade from Sigma Chemical Co. (St. Louis, Mo., USA). $^1$H NMR and $^{13}$C NMR spectra were recorded on Bruker-Avance 400 MHz spectrometer. $CD_3OD$ was used as a solvent. Chemical shifts (δ) were reported in ppm with tetramethylsilane as an internal standard, and J values were given in Hz. High resolution mass spectra (HRMS) were performed on a VG Autospec-3000 spectrometer. Column chromatography was performed by HSCCC (high speed countercurrent chromatography), and the preparative HPLC were used. A waters 2535 Series machine equipped with an Alltech Alltima-$C_{18}$ (4.6×250 mm, 5 μm) was used for HPLC analysis, and the preparative Alltech Alltima-$C_{18}$ column (10×250 mm, 5 μm) was used in sample preparation.

Extraction and Isolation

Figure 1:
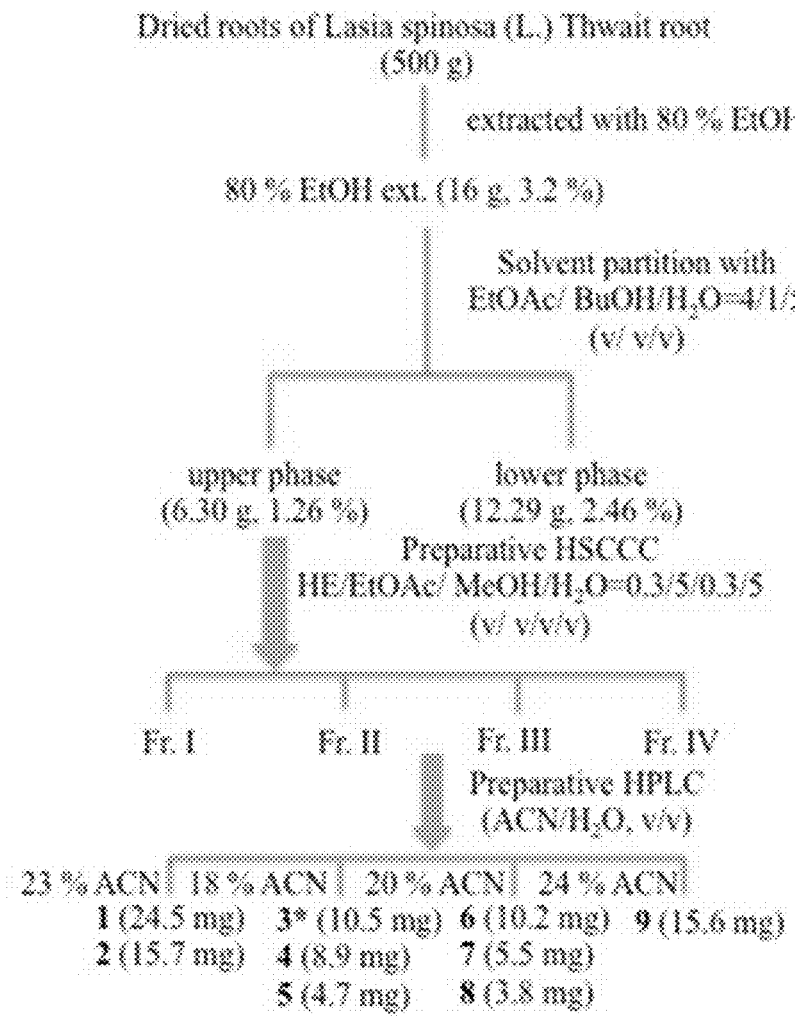
FIG. 1 shows the isolation flow chart of Lasia spinosa (L.) Thwait root. "EtOH" stands for ethanol, "ext." stands extract, "EtOAc" stands for ethyl acetate, "BuOH" stands for n-butanol, "HE" stands for hexane, "MeOH" stands for methanol, "$H_2O$" stands for water extract, and "Fr" stands for fraction.

The dried roots of Lasia spinosa (L.) Thwait root (500 g) were extracted with 80% EtOH by reflex. Upon removal the solvent under reduced pressure, the hydro-alcoholic yielded 16 g of residue. The residue was then suspended in water and partitioned with ethyl acetate/n-butanol/water (EtOAc/BuOH/$H_2O$, v:v:v)=4/1/5 solvent system. The upper layer (6.3 g) was subjected to high-speed counter current chromatography (HSCCC Waters, Germany) with the mixture of hexane/ethyl acetate/methanol/water (HE/EtOAc/MeOH/$H_2O$=0.3/5/0.3/5, v/v/v/v) as the eluting solution so as to afford four fractions (I-IV). Fraction I-IV were further purified using the reverse phase HPLC (Waters system including a 2545 binary gradient module, a 2489 UV/Visible detector, a fraction collector III) on semi-preparative column Preparative RP-$C_{18}$. The isolation flow chart was showed in FIG. 1.

Cytotoxicity Assay

Test compounds were dissolved in dimethyl sulfoxide (DMSO) to make stock solutions and further diluted in culture medium. Human esophageal carcinoma cell lines (KYSE-70, KYSE-150, KYSE-450 and KYSE-520) were cultured in RPMI 1640 or DMEM medium containing 10% fetal bovine serum and 1% antibiotics (Penicillin and strep). $3×10^3$ cells/well were seeded in a 96-well plate and allowed to attach to the plate overnight. After the recovery, cells were treated with 1.56, 3.125, 6.25, 12.5, 25, 50 μg/mL of compounds in culture medium for 48 h. Then, 20 μL of MTT (5 mg/mL stock in PBS) per well was added into the medium (200 μL) and incubated for 4 h at 37° C. Finally, the culture medium was removed and 200 μL of DMSO were added. Absorbance of the solution was measured using microplate reader spectrophotometer (Bio-Rad Laboratories, Inc., Hercules, Calif.) at a wavelength of 570 nm.

Wound Healing Assay

Cells seeded in 12 well-plate at 50% confluence were wounded by scraping across with a sterile plastic tip (1 mL). After being washed with PBS, cells were incubated in a conditioned medium in the absence or presence of tested compounds for various periods of time up to 48 h. The applied concentration of the compounds did not alter the viability of KYSE-150 cells. Cell migration into the wound surface was monitored by Olympus IX71 microscopy and digitally photographed.

Mouse Model

Six to eight weeks old nude female mice weighing about 16-20 g were purchased from the Laboratory Animal Services Center, the Chinese University of Hong Kong, and $2×10^6$ KYSE-150 cells in 200 mL saline were injected subcutaneously into the flanks of the mice. When the tumor volume reached about 100 $mm^3$, the mice were randomly divided into three groups (n=5). The control group was administered with saline, while compound 9 treatment groups were given different doses of 9 (15 or 30 mg/kg, respectively) by intraperitoneal injection. Tumor volume were measured by vernier caliper every two days for 12 days, and calculated according to the formula: Volume=(width)$^2$×length/2. At the end of observation, mice were killed to remove the tumors. Then the samples were fixed in 4% paraformaldehyde and embedded in paraffin. Five-micrometer sections were stained with hematoxylin/eosin according to a standard procedure. Animal protocol was approved by the committee for Care of Laboratory Animals in the School of Chinese Medicine at the Hong Kong Baptist University.

Human equivalent dosage is converted from mouse dosage using the following equation: $D_{human}=D_{mouse}×k$ (k=0.081) (Regan-Shaw et al. (2007). Disclosure thereof is incorporated herein by its entirety.) Therefore, the human equivalent dosage is in a range of 1.215 mg/kg/day to 2.43 mg/kg/day.

Result and Discussion

Figure 2:
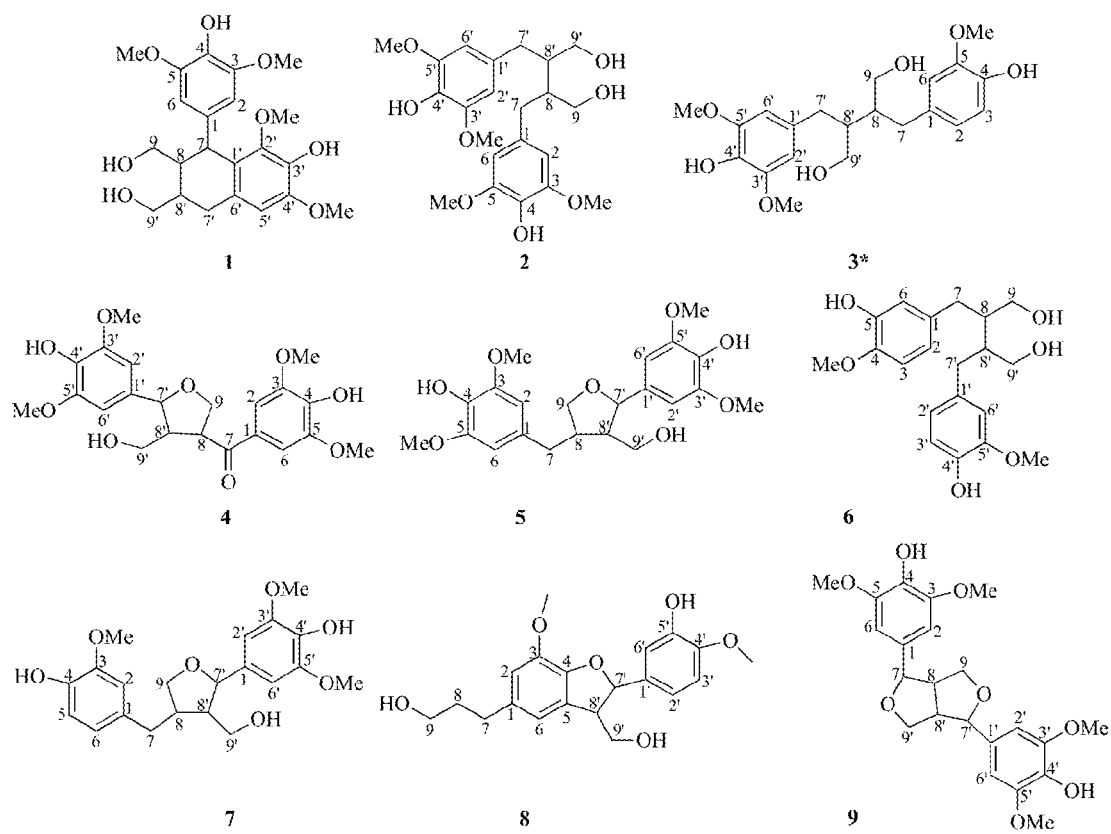
FIG. 2 shows the structure of all the isolated compounds.

The hydro-alcoholic extract of root of Lasia spinosa (L.) Thwait was purified using a column chromatography with HSCCC (high speed countercurrent chromatography), and the preparative HPLC to obtain one novel and eight known lignans. The structures are identified by the $^1$H, DEPT, HSQC, HMBC NMR spectroscopic data as shown in FIG. 2.

Lyoniresinol (1)

yellow gel; $C_{22}H_{28}O_8$, [M+H]$^+$: 421.1872 (Calcd. for 421.1862). $^1$H NMR (400 MHz, $CD_3OD$): δ 6.58 (1H, s, H-2'), 6.38 (2H, s, H-2', 6'), 4.31 (1H, d, J=5.6 Hz, H-7), 3.85 (3H, s, 3'-OMe), 3.73 (3H for each, s, 3,5-OMe), 3.59 (1H, dd, J=10.8, 5.2 Hz, H-9'a), 3.47-3.51 (3H, m, H-9'b and H-9), 3.37 (3H, s, 3-OMe), 2.70 (1H, dd, J=15.2, 4.8 Hz, H-7'a), 2.57 (1H, dd, J=15.2, 11.2 Hz, H-7'b), 1.95-1.99 (1H, m, H-8), 1.59-1.64 (1H, m, H-8'); $^{13}$C NMR (100 MHz, CD$_3$OD): δ 147.58 (s, C-3, 5), 147.25 (s, C-3'), 146.28 (s, C-5'), 137.91 (s, C-1), 137.48 (s, C-4'), 133.11 (s, C-4), 128.78 (s, C-1'), 124.84 (s, C-6'), 106.37 (d, C-2'), 105.47 (d, C-2, 6), 65.38 (t, C-9'), 62.77 (t, C-9), 58.54 (q, 5'-OMe), 55.54 (q, 5-OMe), 55.36 (q, 3-OMe), 55.19 (q, 3'-OMe), 48.47 (d, C-8), 40.90 (d, C-7), 39.48 (d, C-8'), 32.16 (t, C-7').

5,5'-Dimethoxysecoiso-lariciresinol (2)

yellow gel; C$_{22}$H$_{30}$O$_8$, [M+H]$^+$: 423.2074 (Calcd. for 423.2019). $^1$H NMR (400 MHz, CD$_3$OD): δ 6.32 (4H, s, H-2, 2', 6, 6'), 3.74 (12H, s, OMe-3, 3', 5, 5'), 3.65 (2H, dd, J=10.8, 4.8, H$_b$-9, 9'), 3.56 (2H, dd, J=11.2, 5.6, H$_a$-9, 9'), 2.70 (2H, dd, J=13.6, 6.4, H$_b$-7, 7'), 2.52 (2H, dd, J=13.6, 8.8, H$_a$-7, 7'), 1.90-1.88 (2H, m, H-8, 8'); $^{13}$C NMR (100 MHz, CD$_3$OD): δ 147.59 (s, C-3, 3', 5, 5'), 133.02 (s, C-4, 4'), 131.73 (s, C-1, 1'), 105.80 (d, C-2, 2', 6, 6'), 60.87 (t, C-9, 9'), 55.18 (q, OMe-3, 3', 5, 5'), 44.61 (d, C-7, 7'), 35.28 (t, C-8, 8').

2-(4-Hydroxy-3,5-dimethoxybenzyl)-3-(4-hydroxy-3-methoxybenzyl)-1,2-butanediol (3*)

yellow gel; C$_{21}$H$_{28}$O$_7$, [M+H]$^+$: 393.1916 (Calcd. for 393.1913). $^1$H NMR (400 MHz, CD$_3$OD): δ 6.65 (1H, d, H-5'), 6.58 (1H, d, H-2'), 6.54 (1H, dd, J=1.6, 8.0, H-6'), 6.33 (2H, s, H-2, 6), 3.75 (3H for each, s, OMe-3, 5), 3.72 (3H, s, OMe-3'), 3.63 (2H, dd, J=10.8, 4.8, H$_b$-9, 9'), 3.56 (2H, dd, J=11.2, 5.6, H$_a$-9, 9'), 2.68 (2H, dd, J=13.6, 10.8, H$_b$-7, 7'), 2.54 (2H, dd, J=13.6, 8.0, H$_a$-7, 7'), 1.89-1.94 (2H, m, H-8, 8'); $^{13}$C NMR (100 MHz, CD$_3$OD): δ 147.61 (s, C-3, 5), 147.41 (s, C-3'), 144.08 (s, C-1'), 133.04 (s, C-1), 132.47 (s, C-4'), 131.73 (s, C-4), 121.34 (d, C-6'), 114.34 (d, C-5'), 111.96 (d, C-2'), 105.81 (d, C-2, 6), 60.84 (d, C-9), 60.76 (d, C-9'), 55.20 (q, OMe-3, 5), 54.76 (q, OMe-3'), 42.73 (d, C-8), 42.58 (d, C-8'), 35.22 (t, C-7), 34.70 (t, C-7').

(7'S,8S,8R)-4,4'-Dihydroxy-3,3'5,5'-tetramethoxy-7', 9-eproxylignan-9'-ol-7-one (4)

yellow gel; C$_{22}$H$_{26}$O$_9$, [M+H]$^+$: 435.1672 (Calcd. for 435.1655). $^1$H NMR (400 MHz, CD$_3$OD): δ 7.39 (2H, s, H-2, 6), 6.72 (2H, s, H-2', 6'), 4.65 (1H, d, J=8 Hz, H-7'), 4.18-4.29 (3H, m, H-8, 9), 3.92 (6H, s, OMe-3, 5), 3.85 (6H, s, OMe-3', 5'), 3.66-3.69 (2H, m, H-9'), 2.65 (1H, m, H-8'). $^{13}$C NMR (100 MHz, CD$_3$OD): δ 198.94 (s, C-7), 147.84 (s, C-3, 3'), 147.74 (s, C-5, 5'), 141.36 (s, C-4), 134.92 (s, C-4'), 131.51 (s, C-1'), 127.28 (s, C-1), 106.34 (d, C-2, 6), 103.84 (d, C-2', 6'), 84.04 (d, C-7'), 70.15 (t, C-9), 59.99 (t, C-9'), 55.52 (q, OMe-3, 3'), 55.36 (q, OMe-5, 5'), 53.73 (d, C-8'), 48.74 (d, C-8).

5,5'-Dimethoxy-lariciresinol (5)

yellow gel; C$_{22}$H$_{28}$O$_8$, [M+H]$^+$: 421.1868 (Calcd. for 421.1862). $^1$H NMR (400 MHz, CD$_3$OD): δ 6.62 (2H, s, H-2, 6), 6.50 (2H, s, H-2', 6'), 4.77 (1H, d, J=6.4 Hz, H-7'), 4.00 (1H, dd, 8.4, 6.4 Hz, H$_b$-9'), 3.85 (1H, m, H$_b$-9'), 3.83 (3H for each, s, OMe-3, 5), 3.82 (3H for each, s, OMe-3', 5'), 3.75 (1H, dd, J=8.4, 6.0 Hz, H$_a$-9'), 3.66 (1H, dd, J=10.8, 6.4 Hz, H$_a$-9), 2.94 (1H, dd, J=13.6, 4.8 Hz, H$_b$-7'), 2.69-2.78 (1H, m, H-8'), 2.49 (1H, dd, J=13.2, 11.2 Hz, H$_a$-7'), 2.35-2.42 (1H, m, H-8'). $^{13}$C NMR (100 MHz, CD$_3$OD): δ 147.90 (s, C-3, 5) 147.85 (s, C-3', 5'), 134.55 (s, C-4), 133.68 (s, C-4'), 133.48 (s, C-1), 131.42 (s, C-1'), 105.61 (d, C-2', 6'), 102.89 (d, C-2, 6), 82.79 (d, C-7), 72.16 (t, C-9'), 59.12 (t, C-9), 55.38 (q, OMe-3, 5), 55.36 (q, OMe-3', 5'), 52.74 (d, C-8), 42.43 (d, C-8'), 32.77 (t, C-7').

Secoisolariciresinol (6)

yellow gel; C$_{20}$H$_{26}$O$_6$, [M+H]$^+$: 363.1799 (Calcd. for 363.1808). $^1$H-NMR (400 MHz, CD$_3$OD): δ 6.68 (2H, d, J=8 Hz, H-5, 5'), 6.61 (2H, m, H-6, 6'), 6.56 (2H, d, J=7.6 Hz, H-2, 2'), 3.86 (2H, m, H$_b$-9, 9'), 3.75 (6H, s, OMe-3, 3'), 3.60 (2H, m, H$_a$-9, 9'), 2.68 (2H, dd, 13.6, 6.8 Hz, H$_a$-7, 7'), 2.57 (2H, dd, J=13.6, 7.6 Hz, H$_b$-7, 7'), 1.92 (2H, m, H-8, 8'). $^{13}$C NMR (100 MHz, CD$_3$OD): δ 147.40 (s, C-3, 3'), 144.06 (s, C-4, 4'), 132.49 (s, C-1, 1'), 121.32 (d, C-6, 6'), 114.38 (d, C-5, 5'), 111.99 (d, C-2, 2'), 60.73 (t, C-9, 9'), 54.79 (q, OMe-3, 3'), 42.72 (d, C-8, 8'), 32.77 (t, C-7, 7').

5'-Methyoxlariciresinol (7)

yellow gel; C$_{21}$H$_{26}$O$_7$, [M+H]$^+$: 391.1757 (Calcd. for 391.1757). $^1$H NMR (400 MHz, CD$_3$OD): δ 6.82 (1H, d, J=1.6 Hz, H-2'), 6.74 (1H, d, J=8.0 Hz, H-5'), 6.66 (1H, dd, J=8.0, 1.6 Hz, H-6'), 6.64 (2H, s, H-2, 6), 4.79 (1H, d, J=6.8 Hz, H-7'), 4.02 (1H, dd, J=8.4, 6.8 Hz, H$_a$-9), 3.85 (6H, s, OMe-3', 5'), 3.85 (3H, s, OMe-3), 3.80-3.83 (1H, m, H$_a$-9'), 3.75 (1H, dd, J=8.4, 6.4 Hz, H$_b$-9'), 3.49 (1H, dd, J=11.6, 6.8 Hz, H$_b$-9), 2.94 (1H, dd, J=13.6, 4.8 Hz, H$_b$-7), 2.74 (1H, dd, J=5.6, 11.2 Hz, H-8), 2.52 (1H, dd, J=13.2, 11.2 Hz, H$_a$-7), 2.39 (1H, m, H-8'). $^{13}$C NMR (100 MHz, CD$_3$OD): δ 147.84 (s, C-3', 5'), 147.61 (s, C-3), 144.43 (s, C-4), 134.51 (s, C-4'), 133.71 (s, C-1'), 132.12 (s, C-1), 120.76 (d, C-6), 114.80 (d, C-5), 112.00 (d, C-2), 102.85 (d, C-2', 6'), 82.84 (d, C-7'), 72.18 (t, C-9), 59.13 (t, C-9'), 55.36 (q, OMe-3', 5'), 54.98 (q, OMe-3), 52.68 (d, C-8'), 42.41 (t, C-8), 32.26 (t, C-7).

Dihydrodehydrodiconifery Alcohol (8)

yellow gel; C$_{20}$H$_{24}$O$_6$, [M+H]$^+$: 361.1656 (Calcd. for 361.1651). $^1$H NMR (400 MHz, CD$_3$OD): δ 6.97 (1H, d, J=1.6 Hz, H-2'), 6.84 (1H, dd, J=1.6, 8.4 Hz, H-6'), 6.78 (H, d, J=8.0 Hz, H-5'), 6.75 (2H, s, H-2, 6), 5.51 (1H, d, J=6 Hz, H-7'), 3.87 (3H, s, OMe-3'), 3.83 (3H, s, OMe-3), 3.77 (2H, dd, J=7.2, 11.2 Hz, H-9'), 3.59 (2H, t, J=6.4 Hz, H-9), 3.49 (2H, dd, J=6.0, 12.4 Hz, H-8'), 2.63-2.67 (2H, m, H-7), 1.80-1.87 (2H, m, H-8). $^{13}$C NMR (100 MHz, CD$_3$OD): δ 147.68 (s, C-3'), 146.13 (s, C-4), 146.08 (s, C-4'), 143.80 (s, C-3), 135.51 (s, C-1), 133.41 (s, C-1'), 128.48 (d, C-5), 118.30 (d, C-6'), 116.52 (d, C-2), 114.72 (d, C-5'), 112.70 (d, C-6), 109.14 (d, C-2'), 87.58 (d, C-7'), 63.59 (t, C-9'), 60.83 (t, C-9), 55.35 (q, OMe-3'), 54.96 (q, OMe-3), 54.05 (d, C-8'), 34.41 (t, C-8), 31.50 (t, C-7).

Syringaresinol (9)

yellow gel; C$_{22}$H$_{26}$O$_8$, [M+]$^+$: 419.1706 (Calcd. for 419.1706). $^1$H NMR (400 MHz, CD$_3$OD): δ 6.68 (4H, s, H-2, 2', 6, 6'), 4.74 (2H, d, J=4.0 Hz, H-7, 7'), 4.29 (2H, dd, J=6.8, 8.8 Hz, H$_a$-9, 9'), 3.90 (2H, dd, J=3.2, 9.2, H$_b$-9, 9'), 3.86 (12H, s, OMe-3, 3', 5, 5'), 3.17 (2H, m, H-8, 8'). $^{13}$C NMR (100 MHz, CD$_3$OD): δ 147.95 (s, C-3, 3', 5, 5'), 134.81 (s, C-4, 4'), 131.74 (s, C-1, 1'), 103.12 (d, C-2, 2', 6, 6'), 86.22 (d, C-7, 7'), 71.36 (t, C-9, 9'), 55.41 (q, OMe-3, 3', 5, 5'), 54.12 (d, C-8, 8').

All these compounds were evaluated in vitro for their cytotoxic effect using KYSE-70, KYSE-150, KYSE-450 and KYSE-520 cell lines. As shown in Table 1, compound 2 had a strong cell growth-inhibiting effect against KYSE-70, KYSE-150 and KYSE-450 cells for which $IC_{50}$ values are below or near 50 μg/mL. Compound 3 only exerted the cytotoxicity on KYSE-150 cells. Compound 8 can also inhibit the cell growth of KYSE-150 and KYSE-520 cells with $IC_{50}$ value of near 30 μg/mL.

TABLE 1

Cytotoxicity of compounds against Cancer Cell Lines [a]

| Compound | KYSE-150 | KYSE-70 | KYSE-520 | KYSE-450 |
| --- | --- | --- | --- | --- |
| 1 | — | — | — | — |
| 2 | 49.63 | 47.22 | — | 39.21 |
| 3 | 34.48 | — | — | — |
| 4 | — | — | — | — |
| 5 | — | — | — | — |
| 6 | — | — | — | — |
| 7 | — | — | — | — |
| 8 | 31.86 | — | 37.34 | — |
| 9 | — | — | — | — |

[a] Results are expressed as $IC_{50}$ values in μg/mL

Figure 3:
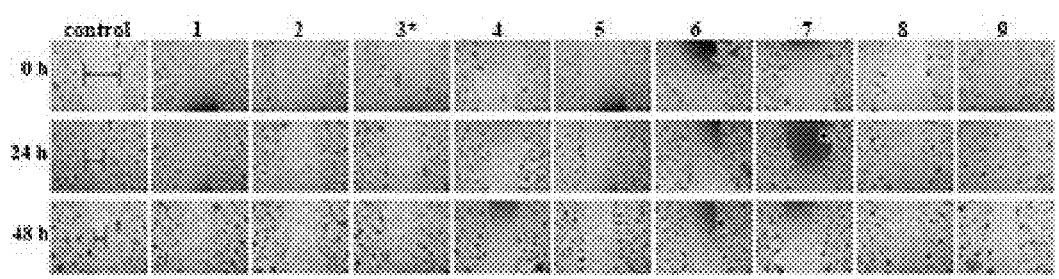
FIG. 3 shows the wound healing assay of five novel compounds on human esophageal carcinoma (KYSE-150) cells; 6.25 μg/mL of compounds 2, 3, 5, 8 and 9, 25 μg/mL of compound 1 and 50 μg/mL of compounds 6,7 were used to treat the cancer cells for 48 h. Original magnification, 5×.

In addition, in vitro wound-healing assay was performed to further examine the inhibitory effect of all isolates on the migratory activity of cancer cells. When treated with isolates, it was found that less migratory KYSE-150 cells were present in the gap after 48 h incubation as compared to that of controls (FIG. 3). The results indicate that the isolated compounds had an anti-migration effect on KYSE-150 cells, and no cytotoxicity.

Figure 4A:
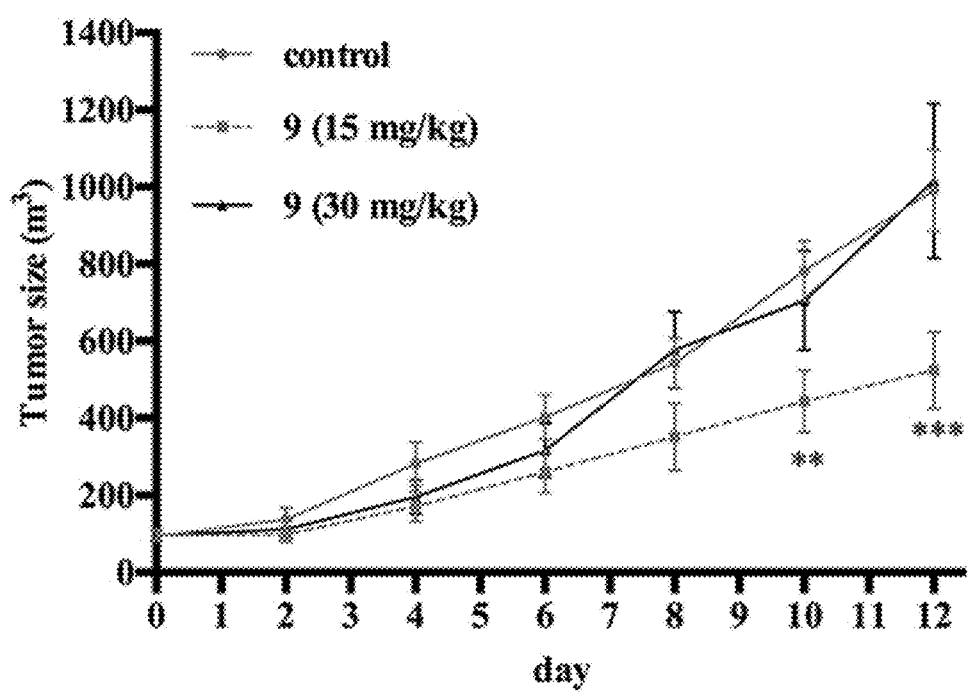
FIG. 4A shows compound 9 suppresses the size of tumor in the tumor xenografts mouse model.
Figure 4B:
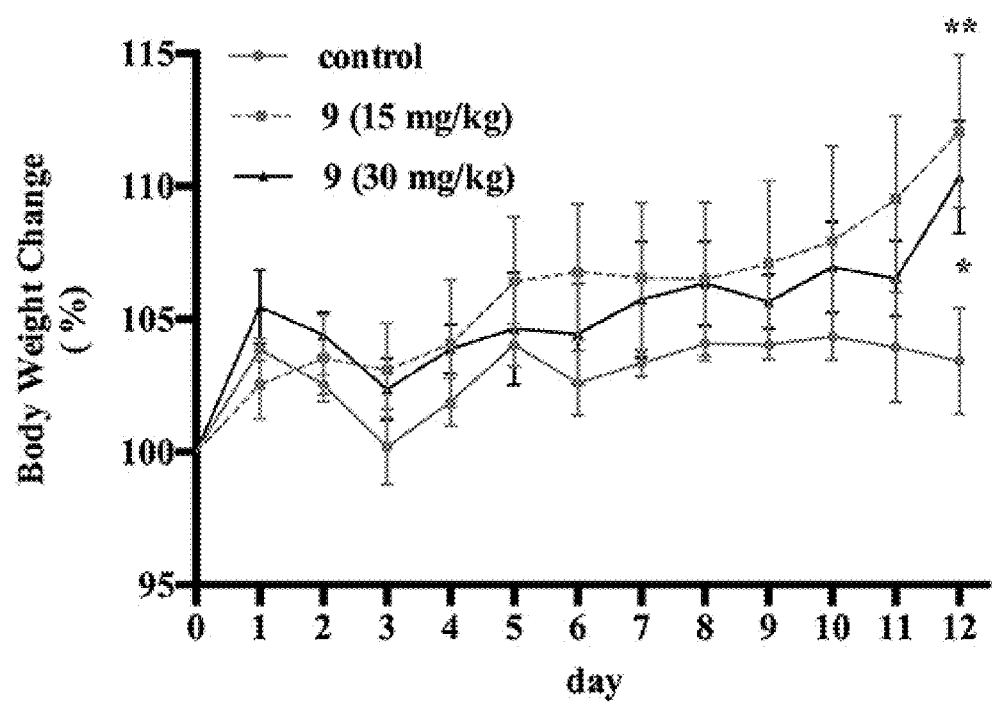
FIG. 4B shows compound 9 suppresses the body weight in the tumor xenografts mouse model.
Figure 4C:
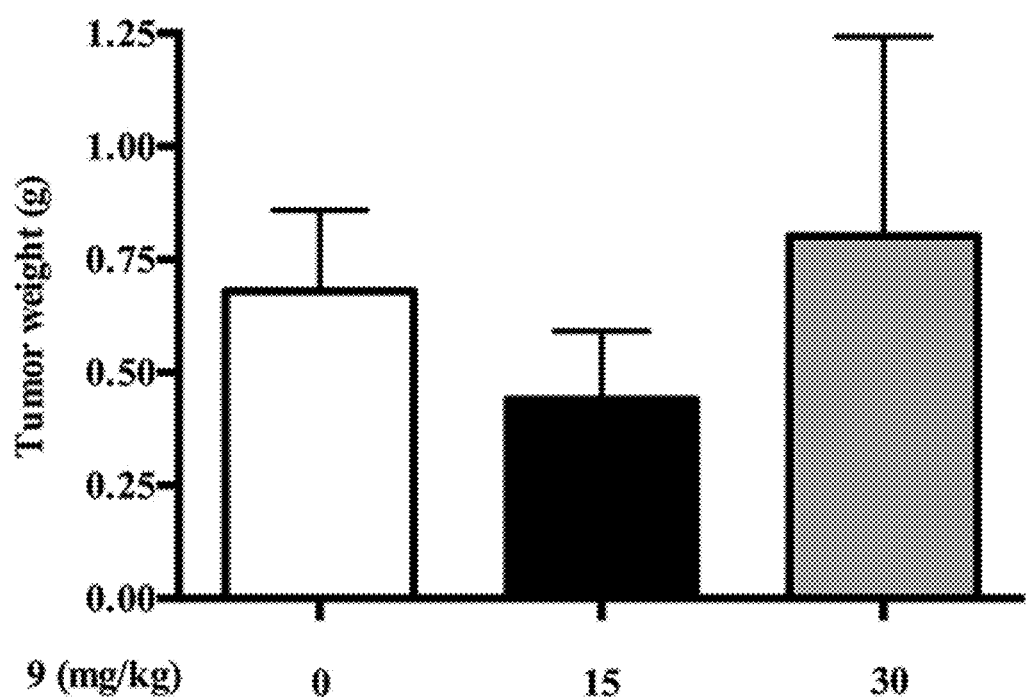
FIG. 4C shows compound 9 suppresses the weight of tumor in the tumor xenografts mouse model.
Figure 4D:
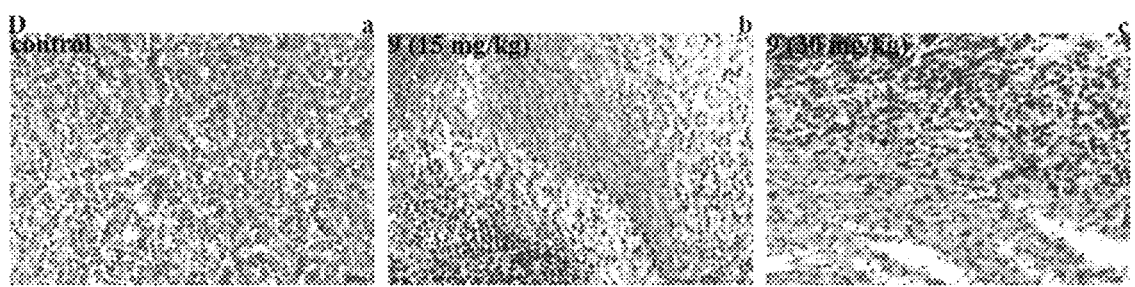
FIG. 4D shows the effects of compound 9 on histological manifestation in tumor tissues (a, control group; b, 9 15 mg/kg group; c, 9 30 mg/kg). The tumor xenograft mice were treated with a vehicle or compound 9 at 15 or 30 mg/kg once a day subcutaneously for 12 days. Tumor size was measured every two days and body weight was measured every day. On day 13, the mice were sacrificed, and tumor weight was measured (n=5, *$p<0.05$, $p<0.01$, *$p<0.001$, ****$p<0.0001$).

The cytotoxic effect of compound 9 was further evaluated in tumor xenograft mouse model. Daily treatments of compound 9 resulted in a significant tumor growth delay, when compared to the control group. Furthermore, compound 9 treatment groups were well tolerated with less body weight loss and no toxic death (FIG. 4A to FIG. 4C). The H&E staining of the tumor tissue in control was orderly and tightly, whereas it was obviously loose and messy in the compound 9 treatment group (FIG. 4D). These results imply that compound 9 attenuated the tumor growth in vivo.

INDUSTRIAL APPLICABILITY

The present invention discloses chemical constituents isolated from the roots of *Lasia spinosa* (L.) Thwait for its medical uses. More particularly, it relates to the bioactive chemical composition of *Lasia spinosa* (L.) Thwait for its anticancer effect.

We claim:

1. A method for inhibiting the growth of an esophageal carcinoma in a subject in need thereof by administering to said subject an effective amount of at least one compound selected from lyoniresinol (1), 5,5'-dimethoxysecoiso-lariciresinol (2), 2-(4-hydroxy-3,5-dimethoxybenzyl)-3-(4-hydroxy-3-methoxybenzyl)-1,2-butanediol (3), (7'S,8S,8R)-4,4'-dihydroxy-3,3'5,5'-tetramethoxy-7',9-eproxylignan-9'-ol-7-one (4), 5,5'-dimethoxysecoiso-lariciresinol (5), 5'-methyoxlariciresinol (7), dihydrodehydrodiconifery alcohol (8) and syringaresinol (9), or a mixture thereof.

2. The method according to claim 1 wherein the compound is administered in an effective amount via intraperitoneal injection.

3. The method according to claim 2 wherein the effective amount is no more than 2.43 mg/kg per day.

4. The method according to claim 1 wherein the subject in need thereof is a human.

5. A method for inhibiting the growth of an esophageal carcinoma in a subject in need thereof by administering to said subject an effective amount of *Lasia spinosa* (L.) Thwait root or an extract from *Lasia spinosa* (L.) Thwait root.

6. The method according to claim 5 wherein the extract is administered via intraperitoneal injection.

7. The method according to claim 5 wherein the subject in need thereof is a human.

* * * * *